United States Patent [19]

King et al.

[11] Patent Number: 5,110,967

[45] Date of Patent: May 5, 1992

[54] CROSSLINKERS AND CHAIN EXTENDERS FOR ROOM TEMPERATURE VULCANIZATION OR CROSSLINKING OF POLYMERS

[75] Inventors: Russell K. King; Chi-long Lee, both of Midland, Mich.

[73] Assignee: Dow Corning Corporation, Midland, Mich.

[21] Appl. No.: 657,018

[22] Filed: Feb. 15, 1991

[51] Int. Cl.$^5$ .............................................. C07F 7/08
[52] U.S. Cl. ...................................... 556/407; 528/12; 528/22
[58] Field of Search .................... 556/407; 528/10, 12, 528/21, 22

[56] References Cited

U.S. PATENT DOCUMENTS

| | | | |
|---|---|---|---|
| 4,465,836 | 8/1984 | Buschhaus | 548/110 |
| 4,680,410 | 7/1987 | Wang | 556/407 X |
| 4,804,771 | 2/1989 | Pepe | 556/407 |

*Primary Examiner*—Arthur Prescott
*Assistant Examiner*—P. Shaver
*Attorney, Agent, or Firm*—Roger H. Borrousch

[57] ABSTRACT

Silicon crosslinkers and chain extenders having at least two heterocyclic Si—N groups per molecule can be used to make compositions which cure in contact with moisture without generating a volatile leaving compound. These heterocyclic Si—N groups are illustrated by the following groups

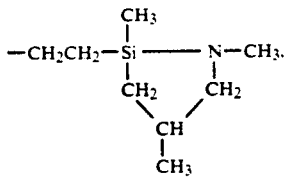

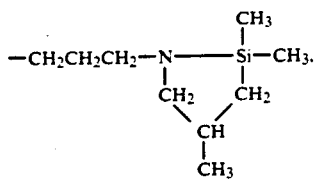

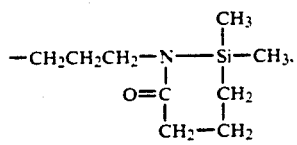

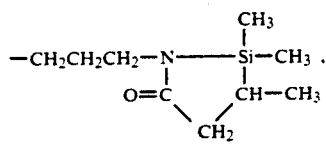

and

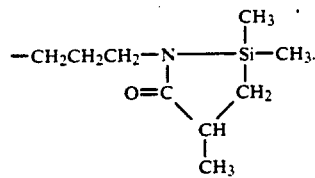

These compositions are useful as coatings for substrates, encapsulants, and sealants.

19 Claims, No Drawings

CROSSLINKERS AND CHAIN EXTENDERS FOR ROOM TEMPERATURE VULCANIZATION OR CROSSLINKING OF POLYMERS

BACKGROUND OF THE INVENTION

1. Field of the Invention

This invention relates to silicon chain extenders and crosslinkers which evolve no volatile by-products upon room temperature vulcanization or crosslinking. They accomplish this by virtue of having groups tethered to the reactive silicon atoms during the curing reaction rather than production of leaving groups.

2. Background Information

Environmental concerns are influencing the direction of product development. In the field of sealants, there is a need to develop products which have very low volatile or leaving materials during the curing process and during the useful life of the cured product. Faced with this problem, the present inventors discovered products which can be used to solve the problem of leaving groups during the curing process and during the useful life of the cured product.

SUMMARY OF THE INVENTION

An object of the present invention is to produce silicon crosslinkers and chain extenders which can be used to make products which cure at room temperature without the evolution of volatile or the production of leachable by-products. This object is accomplished by this invention.

This invention relates to a silicon compound comprising at least one silicon atom to which is bonded at least two heterocyclic Si—N groups having one heterocyclic silicon atom, at least one nitrogen atom, and three to five ring carbon atoms wherein at least one nitrogen atom is bonded to the heterocyclic silicon atom and either a nitrogen atom or the heterocyclic silicon atom is bonded to the silicon atom through a divalent saturated aliphatic hydrocarbon radical.

Another embodiment of this invention relates to compositions comprising a product which is storage stable in a package when protected from moisture but polymerizes when removed from the package and exposed to moisture and comprising a silicon compound comprising at least one silicon atom and at least two heterocyclic Si—N groups as described herein.

DETAILED DESCRIPTION OF THE INVENTION

Elimination of volatile and/or leachable by-products during the curing of silicone compositions and the useful life of the cured products, such as sealants, is accomplished by tethering a hydrolytically unstable group to a central silicon atom via a chain of hydrolytically-stable, covalently-bound atoms bonded to the same silicon atoms.

The compositions of the present invention are silicon compounds which are stable at room temperature when protected from moisture, but polymerize when exposed to moisture in such a manner that no volatile or leachable by-products are produced. They polymerize via a water induced ring opening reaction which yields a silanol. This silanol can either open another ring, creating a siloxane linkage; or condense with another silanol, resulting in a siloxane linkage and a molecule of water. The group bound to a silicon atom which is displaced by the water is "tethered" to the central silicon atom via a bridge of covalently bonded atoms bonded to the same silicon atom. What is meant by tethered is that all of the covalent bonds of the bridging chain are relatively stable to hydrolysis when compared to the silicon leaving group bond.

The compositions of the present invention are chain extenders, those silicon compounds which have two heterocyclic aza groups per molecule, and crosslinkers, those silicon compounds which have at least three heterocyclic Si—N groups per molecule. Some preferred silicon compounds have heterocyclic Si—N groups illustrated by the following formula

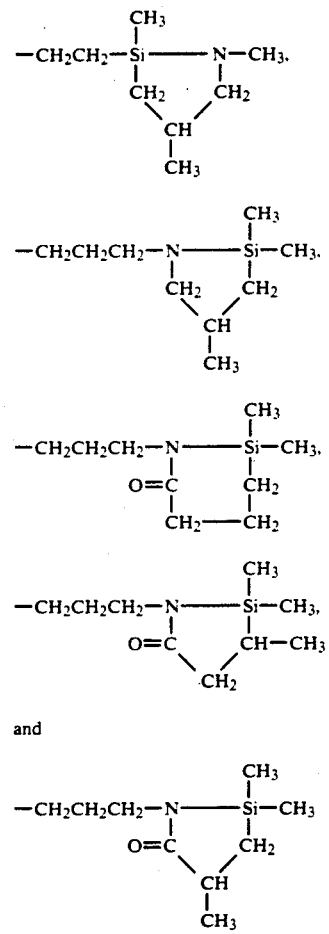

and and the remaining groups bonded to the silicon atoms of the silicon compound are selected from the groups consisting of divalent oxygen atoms, divalent hydrocarbon radicals, and monovalent hydrocarbon radicals.

Chain extenders of the present invention can be illustrated by silicon compounds having a formula selected from the group consisting of ZMe$_2$SiO(Me$_2$SiO)$_y$SiMe$_2$Z, ZMe$_2$Si—X—SiMe$_2$Z, and

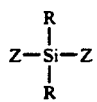

where Z is a heterocyclic Si—N group as previously illustrated, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive.

Crosslinkers of the present invention can be illustrated by silicon compounds having a formula selected from the group consisting of

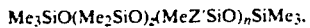

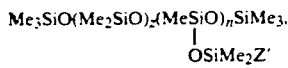

and

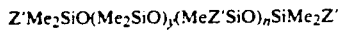

where each Z' is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$.

These silicon compounds, whether chain extender or crosslinker, can be made by reacting silicon compounds having silicon-bonded hydrogen atoms with aliphatically unsaturated azasilacyclopentanes or cyclosilalactams in the presence of a platinum catalyst. This reaction produces the heterocyclic Si—N groups which are the azasilacyclopentanes or cyclosilalactams bonded to the silicon compounds.

The aliphatic unsaturated azasilacyclopentanes have the general formula

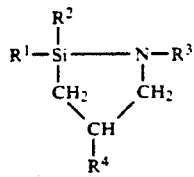

in which each of R$^1$, R$^2$, R$^3$, and R$^4$ is independently selected from the group consisting of a hydrogen atom and a monovalent hydrocarbon radical, where one of R$^1$, R$^2$, and R$^3$ is a monovalent hydrocarbon radical with olefinic unsaturation or acetylenic unsaturation. The monovalent hydrocarbon radicals include methyl, ethyl, propyl, butyl, phenyl, vinyl, allyl, hexenyl, cyclohexyl, tolyl, and isopropyl. Preferably, R$^1$, R$^2$, or R$^3$, when an olefinically or acetylenically unsaturated monovalent hydrocarbon radical, is olefinic and either vinyl, allyl, or hexenyl.

These aliphatically unsaturated azasilacyclopentanes can be prepared from a dialkoxy(chloroalkyl)silane of the general formula

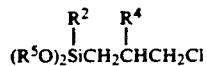

where R$^5$ is an alkyl radical of from 1 to 5 carbon atoms per molecule, including methyl, ethyl, propyl, isopropyl, butyl, isobutyl, and pentyl, by first making a monoalkoxyalkylalkenyl-(3-chloro-2-alkylpropyl)silane of the general formula

by reacting silane (I) with a Grignard reagent of the general formula R$^1$MgX, where X is chlorine, bromine, or iodine, or LiX reagent in the presence of an ether such as diether ether, tetrahydrofuran, or a mixture thereof. One preferred monoalkoxyalkylalkenyl(3-chloro-2-alkylpropyl)silane is methoxymethylvinyl(3-chloro-2-methylpropyl)silane. After the silane (II) is obtained, it can be reacted with acetyl chloride in the presence of a Lewis acid, preferably ferric chloride to make a chloroalkylalkenyl(3-chloro-2-alkylpropyl)silane of the general formula

One preferred chloroalkylalkenyl(3-chloro-2-alkylpropyl)silane is chloromethylvinyl(3-chloro-2-methylpropyl)silane.

These aliphatically unsaturated azasilacyclopentanes can be made by a process described by Speier in U.S. Pat. No. 3,146,250, issued Aug. 25, 1964, where a halogenoalkylhalogenosilane of the formula

is reacted with an amino compound of the formula RNH$_2$, for example, the aliphatically unsaturated azasilacyclopentanes can be made by reacting an alkenylamine with a silane of formula (III). The present invention relates to making azacyclopentanes from specific chloroalkylalkenyl(3-chloro-2-alkylpropyl)silane (formula III) which are new compounds. Speier is hereby incorporated by reference to show the known general reaction of chlorosilanes with an amino compound to make certain nitrogencontaining compounds as discribed herein.

The silicon compounds, whether chain extender or crosslinker, can also be made by reacting silicon compounds having silicon-bonded hydrogen atoms with allyl cyclosilalactams in the presence of a platinum catalyst. This reaction produces the heterocyclic Si—N groups which are the cyclosilalactams bonded to the silicon compounds. The cyclosilalactams can be prepared from chlorosilylbutanoic acid precursors and chlorosilyl-propanoic acid precursors.

These cyclosilalactams are represented by the general formulae

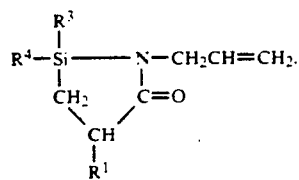  (A)

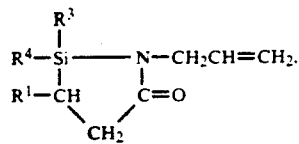  (B)

and

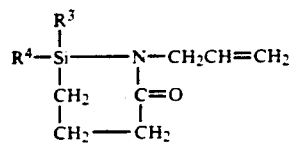  (C)

in which each of $R^1$, $R^3$, and $R^4$ is independently selected from the group consisting of a hydrogen atom and a monovalent hydrocarbon radical. The monovalent hydrocarbon radicals include methyl, ethyl, propyl, butyl, phenyl, vinyl, allyl, hexenyl, cyclohexyl, tolyl, and isopropyl. Preferably, $R^1$, $R^3$, or $R^4$ are methyl.

The cyclosilalactams of the present invention can be prepared by a method similar to the above method described by Mironov et al in "Synthesis of Silalactams", Khim. Geterotsikl. Soedim., (Chemistry of Heterocyclic Compounds), 1968, Vol. 6, p. 1124. However, the cyclosilalactams of the present invention are prepared by the following methods.

The preparation of cyclosilalactam of formula (A) is made by sequentially reacting a diorganosilyl ester of methacrylic acid having the formula $$CH_2=C(CH_3)-C(=O)-O-Si(R^3)(R^4)-H$$

with a platinum catalyst exemplified by chloroplatinic acid, or complexes of chloroplatinic acid with sym-divinyltetramethyldisiloxane, and thionyl chloride ($SOCl_2$) with heating. The removal of the by-products which can be both solids and liquids produces a chlorosilylpropanoic acid precursor, namely 3-chlorodiorganosilyl-2-methylpropanoic acid chloride of the formula

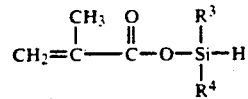

which is then reacted with allylamine producing a cyclosilalactam of formula (A).

The cyclosilalactams of formula (B) and (C) can be prepared by a method which produces both at the same time. A chlorosilane of the formula

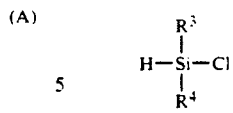

is reacted with trimethylsilyl ester of vinylacetic acid in the presence of a platinum catalyst such as described above with heating. After the reaction, thionyl chloride is slowly added to the solution to give a mixture of chlorosilabutanoic acid chloride represented by the general formula

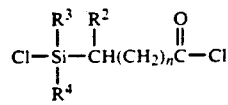

where $R^2$ is a hydrogen atom or methyl radical and n is 1 or 2. The mixture of chlorosilylbutanoic acid chlorides preferably have the formulae

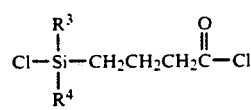

and

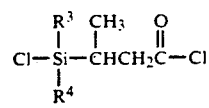

The addition of allylamine to the above mixture of chlorosilanes produces a mixture of cyclosilalactams of formula (B) and (C).

The above mixture can also be made by heating dimethylsilyl ester of vinylacetic acid, i.e., $HMe_2SiOC(O)CH_2CH=CH_2$, in the presence of a platinum catalyst such as described above, followed by reacting with thionyl chloride.

The above aliphatically unsaturated azasilacyclopentanes and cylosilalactams are reacted with silicon-bonded hydrogen containing compounds in the presence of a platinum catalyst, preferably with heating. The silicon-bonded hydrogen containing compounds can be illustrated by the following $HMe_2SiOSiMe_2H$, $(MeHSiO)_4$, $(MeHSiO)_5$, $HMe_2SiO(Me_2SiO)_{98}SiMe_2H$, $Me_3SiO(Me_2SiO)_3(MeHSiO)_5SiMe_3$, $(HMe_2SiO)_3SiMe$, $(HMe_2SiO)_4Si$, $((HMe_2SiO)_3SiO_{1/2})_2((HMe_2SiO)_2SiO)_4$, and $(HSiO_{3/2})_{12}$, in which Me is methyl.

A chain extender may be prepared as follows:

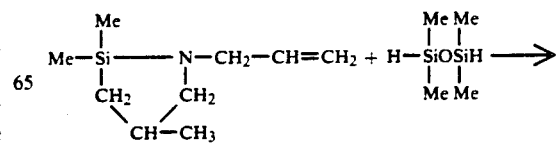

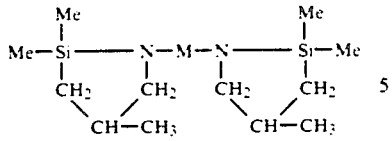

(Chain Extender I)

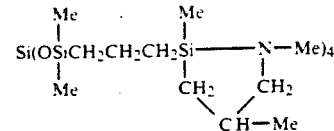

(Crosslinker I)

(reaction is carried out in the presence of a platinum catalyst and (This reaction takes place in the presence of a platinum catalyst)

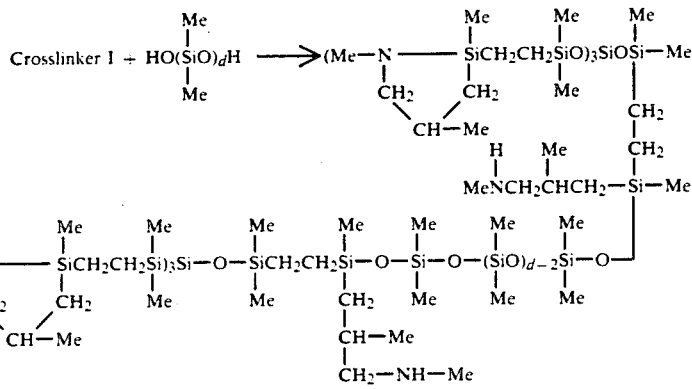

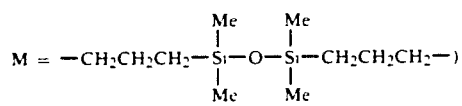

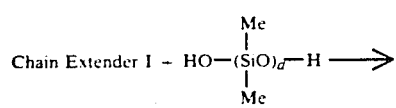

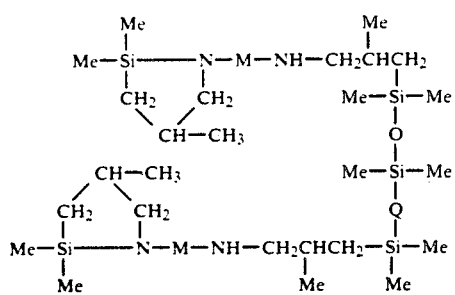

(d is an average value of at least one and Q is —O(Me$_2$SiO)$_{d-1}$—). The above chain extending reaction can react further as long as there are heterocyclic Si—N groups and silanols available. This chain extending reaction can take place in the presence of crosslinking reactions. From the above illustration, there are no volatile compounds produced.

An example of a crosslinker, which is reacted with a hydroxyl endblocked polydimethylsiloxane, is prepared as follows:

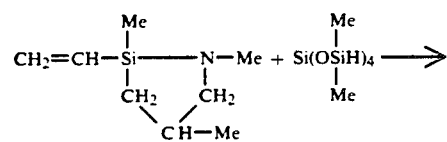

These crosslinkers can further react with moisture or other silanol functionality to cure compositions. By using combinations of crosslinkers and chain extenders one can vary the resulting properties of the cured product. Additionally, the cure properties can be varied by the nature of the silanol functional polysiloxanes which are used.

The heterocyclic Si—N groups of the chain extenders and crosslinkers of this invention are believed to react in the following manners:

(1) with water

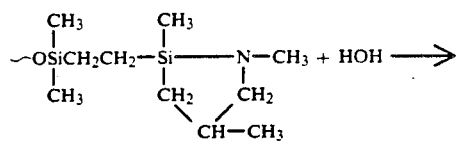

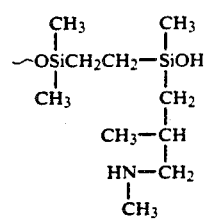

or,

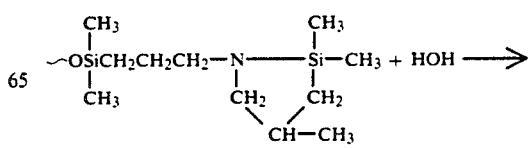

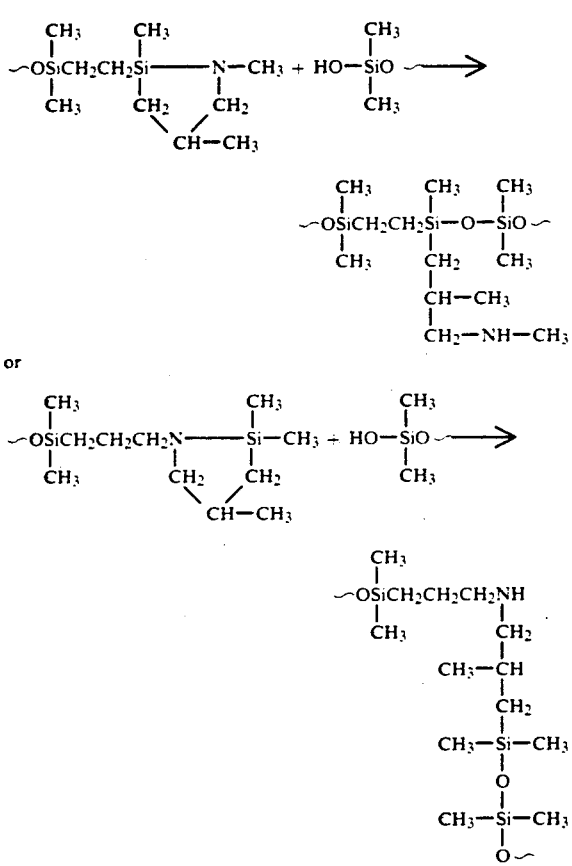

The above reactions are illustrative only using preferred heterocyclic Si—N groups.

The compositions, which are storage stable in a package when protected from mositure but polymerize and cure when removed from the package and are exposed to moisture of the atmosphere, can be made by mixing crosslinkers (as described herein) with polyorganosiloxanes having silicon-bonded hydroxyl groups (silanols, Si—OH) or by mixing crosslinkers and chain extenders (as described herein) with polyorganosiloxanes having SiOH groups. These compositions can contain fillers and other ingredients which are useful in the preparation of sealants and are not harmful to the chain extenders and crosslinkers of this invention, such as where the additive might cause premature reaction of the chain extender or the crosslinker and thus causing gellation in the package or causing it not to be available for reaction when the composition is removed from the package and is exposed to mositure, preferably the atmospheric moisture. Fillers which may be useful are illustrated by reinforcing silica, surface treated reinforcing silica, calcium carbonate, and carbon black. Curing catalysts which might be useful are illustrated by dibutyltin diacetate, dibutyltin dilaurate, tetrabutyl titanate, tetraisopropyl titanate, stannous octoate, and 2,5-di-isopropoxy-bis-ethylacetoacetate titanium.

Compositions which are storage stable in one package when protected from moisture but polymerize and cure when removed from the package and exposed to moisture of the atmosphere can be made by mixing (A) crosslinkers of the present invention having a formula selected from the group consisting of $Si(OSiMe_2Z')_4$, $RSi(OSiMe_2Z')_3$, $[-(MeZ'SiO)_x-]$, $Me_3SiO(Me_2SiO)_x(MeZ'SiO)_nSiMe_3$, $Me_3SiO(Me_2SiO)_x(MeSiO)_nSiMe_3$
         |
         $OSiMe_2Z'$ and $Z'Me_2SiO(Me_2SiO)_x(MeZ'SiO)_nSiMe_2Z'$ where each $Z'$ is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$ with (B) a silanol functional siloxane selected from the group consisting of a linear polydiorganosiloxane represented by the following formula $HO(R_2SiO)_dH$ where R is a monovalent hydrocarbon radical, such as methyl, ethyl, propyl, hexyl, vinyl, phenyl, and 3,3,3-trifluoropropyl and d has an average value of from 1 to 1,000; with a silicone resin represented by the formula $(SiO_2)_f(RSiO_{1.5})_g(R_2SiO)_h(R_3SiO_{0.5})_i(OH)_j$ where R is defined above and the values of f, g, h, and i being such that the ratio of R/Si is in the range of 0.5 to 1.8 and the value of j is such that there is at least two silicon-bonded hdyroxyl groups per molecule; and mixtures thereof. The molar ratio of the heterocyclic Si—N group per silanol group (Si—OH) is in the range of 2:1 to 50:1.

A two package composition can be prepared by using (I) the one package composition as one part and (II) as a second package silanol functional siloxane as described above for (B). These are combined when cure is desired by mixing (I) and (II) in a ratio sufficient to provide one silanol function from (II) for each remaining (unreacted) heterocyclic Si—N group in (I). When (I) and (II) are combined in these ratios, there is no need to depend upon atmospheric moisture to cause the mixture of (I) and (II) to form a cured product. Some of the silanol groups in (II) can be replaced by water providing the OH from either the silanol functional siloxane or the water so that the ratio of (I) and (II) when mixed will cure without the need for atmospheric moisture. Silanol functional siloxane of (II) can be a mixture of different molecular weight siloxanes.

The following examples are presented for illustrative purposes and should not be construed as limiting the invention which is properly delineated in the claims. In the following examples, "part" and "parts" are respectively "part by weight" and "parts by weight", Me = methyl. Ph = phenyl.

EXAMPLE 1

Reaction of 1,1,3,3-tetramethyldisiloxane with 1,2,4-trimethyl-1-vinyl-2-aza-silacyclopentane The 1,2,4-trimethyl-1-vinyl-2-aza-silacyclopentane was prepared as follows. To a solution of 50.0 g (254 mmol) of dimethoxy-methyl(3-chloro-2-methylpropyl)-silane in 250 ml of diethyl ether in a three-necked, 1 L (liter) round-bottom flask fitted with a mechanical stirrer, nitrogen inlet, and addition funnel was added over one hour, a solution of 290 ml (290 mmol) of 1M (molar) vinyl magnesium bromide in tetrahydrofuran (THF). The reaction was allowed to stir overnight under a nitrogen atmosphere at room temperature and the slightly yellowish liquid was decanted from the solids. The solvents were removed at 40° C. and 9 mmHg to yield 68.09 g of a yellow liquid with considerable amounts of solids. To this was added 50 ml of benzene and the salts were removed by filtration through a course glass frit funnel. The collected solids were washed with two 30 ml portions of benzene. The combined organic fractions were stripped at 50° C. and 9 mmHg to yield 40.19 g of liquid with a small amount of salts. The results of gas chromatography-mass spectroscopy (GC-MS) showed the following composition of the liquid:

A. 1.9 wt %

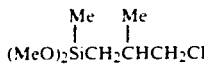

B. 92.9 wt %

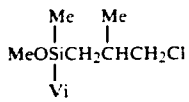

C. 3.3 wt %

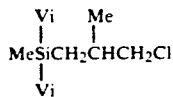

D. 0.9 wt %

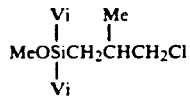

3.1 wt % of 9 unidentified impurities at an order of magnitude lower level.

The mass spectra was used to identify these compounds and the results were:

For B compound: 192, not observed, M+; 165(10), M—Vi; 137(10), NA; 121(210), (MeO)ViClSi+; 109(230), (MeO)MeClSi+; 101(780), (MeO)MeViSi+; 56(1000), $C_4H_8{}^+$ where data are presented as charge (m/e), (relative intensity).

For C compound: 188, not observed, M+; 161(8), M—Vi; 117(280), $Vi_2ClSi^+$; 105(284), MeViSi+; 97(489), $Vi_2MeSi^+$; 56(1000), $C_4H_8{}^+$.

For D compound: 204, not observed, M+; 177(10), M—Vi; 121(290), (MeO)ViClSi+; 113(620), (MeO)-$Vi_2Si^+$; 56(1000), $C_4H_8{}^+$.

The $^{29}Si$ nuclear magnetic resonance(NMR) had one major peak at 6.63 ppm relative to tetramethylsilane. The crude product was purified by short path distillation. The fraction boiling at 75° C. at 6 mmHg weighed 28.22 g (58% yield) and was identified as compound B, methoxymethylvinyl(3-chloro-2-methylpropyl)silane.

Chloromethylvinyl(3-chloro-2-methylpropyl)silane was prepared as follows. A mixture of 28.00 g (143.3 mmol) of compound B in 15.5 ml (17.10 g, 217.9 mmol, 1.5 eq) of acetyl chloride was allowed to sit at ambient temperature for 12 hours. A slight exotherm was noted. The low boiling material was removed by distillation and the product distilled at 88° C. to 90.5° C. and 30 mmHg to give 25.2 g of material (88% yield). The product was chloromethylvinyl(3-chloro-2-methylpropyl)silane as was identified by $^{13}C$ NMR: 134.79 and 134.73 and 134.68 (1:2:1, 1.67), SiVi; 52.93 (1.00), $CH_2Cl$; 31.51 and 31.48 (0.83), CH; 22.88 and 22.84 (0.97), CHMe; 20.13 and 20.10 (1.01), $SiCH_2$; 0.59 and 0.54 (0.68), SiMe and by $^{29}Si$ NMR: 17.81 and 17.78 (1:1) where data are presented as ppm (relative intensity).

Methylamine was condensed into a 1 L round-bottom flask and distilled from sodium. To 490 ml (340 g, 11 mol) of methylamine was slowly added 309.8 g (1.57 mol) of chloromethylvinyl(3-chloro-2-methylpropyl)silane, which resulted in two phases. The two phase system was transferred to a Parr reactor and heated at 110° C. and 230 psig for 10 hours. The reaction mixture was cooled to −10° C., transferred to a 2 L round-bottom flask and 400 ml of cold pentane was added. The layers were separated, and the upper organic phase concentrated. After concentration, some ammonium salts had precipitated. These salts were removed by filtration and the product purified by distillation at reduced pressure to yield about 160 g (60% yield) of aza-silacyclopentane with a small amount of ammonium salts. The distilled product was 97% pure 1,2,4-trimethyl-1-vinyl-2-aza-silacyclopentane with two major higher boiling impurities (about 1 wt % each) and numerous minor higher boiling impurities. The GC-MS data was: 1,2,4-Trimethyl-1-vinyl-2-aza-silacyclopentane, Retention Time 2.00 min; 155 (365), M+; 154 (243), M+—H; 140(97), M+—Me; 126 (113), M+—Vi; 113 (962), M+—$C_3H_7$; 112 (1000), M+—$C_3H_7$; 89 (396), MeVi-$SiN=CH_2{}^+$; 71 (465) MeViSiH+. The $^{13}C$ NMR spectra was: 138.23 and 137.98, terminal vinyl; 132.86 and 137.98, internal vinyl; 62.19 and 61.92, N—$CH_2$; 33.93 and 33.80, methine; 32.09 and 32.06, NMe; 21.48 and 21.54, CHMe; 21.23 and 20.95 Si—$CH_2$; −3.43 and −4.29, SiMe. The $^{29}Si$ NMR had peaks at 6.229 and 6.039 relative to tetramethylsilane.

A dry 100 ml three-necked round-bottom flask fitted with a thermometer, condenser, and addition funnel was charged with 17.00 g (126.6 mmol) of tetramethyldisiloxane (not dried). The addition funnel was charged with 51.5 g (331.6 mmol) of the 1,2,4-trimethyl-1-vinyl-2-aza-silacyclopentane prepared above. Chloroplatinic acid in isopropanol (9 uL, 10% solution) and a portion of the 1,2,4-trimethyl-1-vinyl-2-aza-silacyclopentane were added to the tetramethyldisiloxane and the mixture was heated to 120° C. The remainder of the 1,2,4-trimethyl-1-vinyl-2-aza-silacyclopentane was added dropwise over a 15 minute period. A mild (ca. 15° C.) exotherm was observed. After the addition, infrared analysis (IR) indicated that ca. 75% of the SiH had been consumed. This did not change after heating at 120° C. for 90 min. The temperature was gradually increased to 160° C. and the IR indicated the slow consumption of all the SiH after about 40 min. The product was purified by distillation. (88% mass balance). The fractions of the distillation were as follows in Table I:

TABLE I

| FRACTION NO. | BATH TEMPERATURE °C. | PRESSURE mm Hg | HEAD TEMPERATURE °C. | WEIGHT grams | FRACTION IDENTITY |
|---|---|---|---|---|---|
| 1 | 90 | 30 | 36 | 12.12 | (1) |
| 2 | 90->142 | 30->0.1 | 72-106 | 2.15 | (2) |
| 3 | 142->150 | 0.1 | 106-120 | 1.45 | (3) |
| 4 | 150 | 0.1 | 130->140 | 4.60 | (4) |
| 5 | 150->170 | 0.1 | 142-150 | 31.5 | (5) |
| POT | — | — | — | 8.50 | (6) |

(1) = 1,2,4-trimethyl-1-vinyl-2-aza-silacyclopentane
(2)-(4) = unknowns
(5) = disiloxane product as defined below
(6) = partially hydrolyzed disiloxane product The following disiloxane product (Fraction No. 5) was obtained in a 31.5 g amount

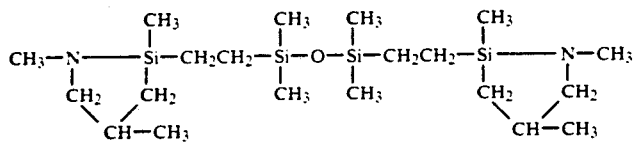

The $^{29}$Si NMR (0.04M Cr(acetylacetonate)$_2$, 6.0 sec delay): Main Fraction: 18.97 and 18.80 (1), cyclic silazane Si's; 8.14, 8.06, 7.96, and 7.88 (1.2) disiloxane Si's. Pot Residue: 18.94 and 18.78 (1), cyclic silazane Si's, 8.14-7.90 broad (1.95), original disiloxane Si's and disiloxane Si's from hydrolyzed and condensed ring.

The mass spectrum was [m/e(int)]: 444(16), M$^+$; 429 (8), M$^+$—Me; 316 (25), ring—CH$_2$CH$_2$SiMe$_2$OSiMe$_2$CH$_2$CH$_2$$^+$; 214 (50), ring—CH$_2$CH$_2$SiMe$_2$$^+$; 156 (16), ring—CH$_2$CH$_2$$^+$; 128 (100), ring$^+$.

EXAMPLE 2

Reaction of 1,1,3,3-Tetramethyldisiloxane with 1,1,4-Trimethyl-2-allyl-2-aza-silacyclopentane The 1,1,4-trimethyl-2-allyl-2-aza-silacyclopentane was prepared as follows. Chlorodimethyl(3-chloro-2-methylpropyl)silane (100 g, 0.54 mol) was slowly added to 211.73 g (3.71 mol, 6.87 eq) of undistilled allyl amine resulting in an exothermic reaction. This reaction mixture was stirred at room temperature for 15 hours, heated to reflux at atmospheric pressure for 72 hours, and heated to 120° C. under about 50 psig pressure for 16 hours. The following GC-MS ratios shown in Table II exemplified the reactions progression and the spectra observed were as shown.

TABLE II

| RETENTION TIME, MIN | 15 HOURS 20° C. | 24 HOURS REFLUX | 72 HOURS REFLUX | 16 HOURS 120° C. | COMPOUND |
|---|---|---|---|---|---|
| 2.70 | 0.0 | 3.9 | 21.3 | 71.9 | E |
| 2.82 | 0.0 | 1.0 | 1.1 | 0.9 | F |
| 3.20 | 50.4 | 11.0 | 4.1 | 0.0 | G |
| 5.19 | 29.5 | 63.0 | 40.2 | 0.0 | H |
| 8.46 | 20.0 | 8.8 | 8.1 | 2.4 | I |
| 9.58 | 0.0 | 9.3 | 10.1 | 6.1 | J |
| 10.58 | 0.0 | 3.1 | 15.1 | 18.7 | K |

Compound E was 1,1,4-trimethyl-2-allyl-2-aza-silacyclopentane and the spectra was 169 (819), M$^+$; 154 (1326), M$^+$—CH$_3$; 142 (1074), M$^+$—Vi; 127 (375), M$^+$—C$_3$H$_6$; 126 (354), M$^+$—C$_3$H$_7$; 100 (784), M-69; 86 (8734), Me$_2$SiN=CH$_2$$^+$; 59 (10000), Me$_2$SiH$^+$. Compound F was not determined.

Compound G was chlorodimethyl(3-chloro-2-methylpropyl)silane and the spectra was 184 (0), M$^+$; 169 (233), M$^+$—Me; 137 (292), M$^+$—47; 113 and 115 (2459 and 1991), Cl$_2$MeSi$^+$; 93 (9786), ClMe$_2$Si$^+$; 56 (10000), C$_4$H$_8$.

Compound H was allylaminodimethyl(3-chloro-2-methylpropyl)silane and the spectra was 205 (10), M$^+$; 190 (79), M$^+$—Me; 170 (153), M$^+$—Cl; 149 (618), M$^+$—C$_4$H$_8$; 134 and 136 (1263 and 508), M$^+$—CH$_3$—C$_4$H$_8$; 120 and 122 (1250 and 625), unassigned; 114 (10000), CH$_2$=CHCH$_2$NHSiMe$_2$$^+$; 98 (4709), unassigned; 93 and 95 (4999 and 1948), ClMe$_2$Si$^+$.

Compound I was 1,1,3,3-tetramethyl-1,3-bis(3-chloro-2-methylpropyl)disiloxane and the spectra was 314 (0), M$^+$; 187 and 189 (2045 and 1291), ClMe$_2$SiOSiMeCl$^+$; 167 and 169 (10000 and 3897), ClMe$_2$SiOSiMe$_2$$^+$.

Compound J was 1,1,3,3-tetramethyl-1-(3-chloro-2-methylpropyl)-1-(3-allylamino-2-methylpropyl)disiloxane and the spectra was 335 (0), M$^+$; 320 (52), M$^+$—Me; 167 and 169 (1216 and 463), ClMe$_2$SiOSiMe$_2$$^+$; 70 (10000), CH$_2$=CHCH$_2$NH=CH$_2$$^+$.

Compound K was 1,1,3,3-tetramethyl-1,3-bis(3-allylamino-2-methylpropyl)disiloxane and the spectra was 356 (0), M$^+$; 170 (1017), CH$_2$=CHCH$_2$NHCH$_2$CH(CH$_3$)CH$_2$SiMe$_2$$^+$; 169 (1177), peak 170-H; 70 (10000), CH$_2$=CHCH$_2$NH=CH$_2$$^+$.

Upon cooling the product of the reaction, a two phase system resulted. The upper phase weighed 111.85 g and contained most of the product 1,1,4-trimethyl-2-allyl-2-aza-silacyclopentane. The lower phase weighed 177.12 g and was an amber viscous liquid. This lower phase was concentrated at atmospheric pressure with a pot temperature of 120° C. to 122 g. Another 4.0 g of the upper phase was separted upon cooling. The combined product phases were distilled under vacuum. After a slow evolution of allylamine, the product codistilled with an ammonium salt at 78° C. and 30 mmHg. Filtration gave 51.63 g (56% yield) of essentially pure 1,1,4- trimethyl-2-allyl-2-aza-silacyclopentane. The $^{13}$C NMR was: 138.13, vinyl; 114.39, vinyl; 58.98, allyl CH$_2$; 50.31, ring CH$_2$N; 31.88, CH; 21.94 and 21.50, SiCH$_2$ and C-Me; 0.22 and −0.76, SiMe. The $^{29}$Si NMR spectra had one peak at 15.56 ppm relative to tetramethylsilane.

A dry 100 ml three-necked, round-bottom flask fitted with a thermometer, condenser, and addition funnel was charged with 12.00 g (89.3 mmol) of tetramethyldisiloxane (not dried). The addition funnel was charged with 36.31 g (214.4 mmol) of 1,1,4-trimethyl-2-allyl-2-aza-silacyclopentane. 0.02 Gram of a platinum catalyst of the formula

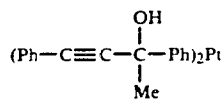

and a portion of 1,1,4-trimethyl-2-allyl-2-aza-silacyclopentane were added to the tetramethyldisiloxane and the mixture was heated to 120° C. The remainder of 1,1,4-trimethyl-2-allyl-2-aza-silacyclopentane was added dropwise over a 24 minute period. The temperature was gradually increased to 160° C. IR indicated complete comsumption of the SiH after about 60 min. After distilling of the excess 1,1,4-trimethyl-2-allyl-2-aza-silacyclopentane and a small lower boiling fraction (0.4 g. B.P. 140°-170° C., 0.1 mmHg), the disiloxane product was purified by distillation at 0.1 mmHg, 170°-180° C. to yield 27.27 g (64.5%) of product. The pot residue weighed 6.5 g and was identified as partially hydrolyzed disiloxane product. The $^{29}$NMR (CDCl$_3$) was: 14.61 and 7.62. The $^{13}$C NMR (CDCl$_3$) was: 59.1, 51.5, 32.3, 24.0, 22.0, 21.8, 17.7, 1.0, −0.8. The mass spectrum was [m/e(int)]: 472 (29), M$^+$; 457, (7), M$^-$—Me; 330 (6), ring—CH$_2$CH$_2$CH$_2$SiMe$_2$OSiMe$_2$CH$_2$CH$_2^+$; 302 (12), ring—CH$_2$CH$_2$CH$_2$SiMe$_2^-$; 142 (1000), ring=CH$_2$. The disiloxane product had a formula

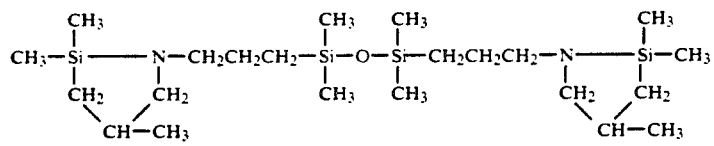

EXAMPLE 3

Reaction of Tetrakis(dimethylsiloxy)silane with 1,1,4-Trimethyl-2-allyl-2-aza-silacyclopentane Three preparations were done by reacting 1 g (3.0 mmol) of tetrakis(dimethylsiloxy)silane with 0.52 g (3.0 mmol), 1.04 (6.1 mmol), and 2.07 (12.2 mmol) respectively of 1,1,4-trimethyl-2-allyl-2-aza-silacyclopentane and a small amount of the platinum catalyst of Example 2 in glass vials which were sealed and then heated as described in Example 2 until the reaction occured. The molar ratio of 1,1,4-trimethyl-2-allyl-2-aza-silacyclopentane to Si—H of 1:1 resulted in a conversion of the Si—H of 49%. The molar ratio of 1,1,4-trimethyl-2-allyl-2-aza-silacyclopentane to Si—H of 2:1 resulted in a conversion of the Si—H of 71%. The molar ratio of 1,1,4-trimethyl-2-allyl-2-aza-silacyclopentane to Si—H of 4:1 resulted in a conversion of the Si—H of 83%. The heterocyclic Si—N groups bonded to the tetrakis(dimethylsiloxy)silane had the following formula

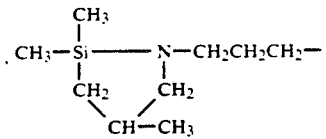

and the silicon compound with the heterocyclic Si—N groups had a formula

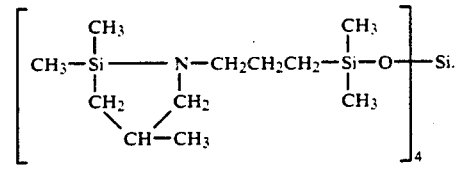

EXAMPLE 4

Reaction of Tetrakis(dimethylsiloxy)silane with 1,1,4-Trimethyl-2-allyl-2-aza-silacyclopentane A 50 ml round-bottom flask fitted with an addition funnel containing 28.33 g (182.5 mmol) of 1,1,4-trimethyl-2-allyl-2-aza-silacyclopentane was charged with 15.00 g (45.6 mmol) of tetrakis(dimethylsiloxy)silane and 0.023 g of the platinum catalyst as described in Example 2. An approximate 3 g portion of 1,1,4-trimethyl-2-allyl-2-aza-silacyclopentane was added and the mixture was warmed to 120° C. The remainder of 1,1,4-trimethyl-2-allyl-2-aza-silacyclopentane was added over an approximate 10 minute period. IR indicated some residual SiH. Another 3.0 g portion of 1,1,4-trimethyl-2-allyl-2-aza-silacyclopentane was added and the reaction was heated to 170° C. for two hours. IR indicated complete disappearance of the SiH. A vacuum distillation head was attached and the product stripped until no volatiles were evolved at 170° C. and 0.04 mmHg. The weight of the isolated product material was 41.3 g (95%). The $^{13}$C NMR (CDCl$_3$) was: 138.8, 138.2, 133.8, 132.1, 62.2, 62.1, 34.1, 34.0, 32.1, 32.05, 22.2, 22.1, 22.02, 21.95, −3.3, −3.9, −4.0. The $^{29}$Si NMR (CDCl$_3$) was: 19.1 and 18.6 (0.73); 10.2-8.8 (4 peaks)(1.00); 6.5 and 6.3 (0.09); −5.4 to −6.4 m(0.13); −104 to −105 m(0.27). This implied that substitution was between 73 to 88% complete (i.e. functionally between 3.52 to 2.92). The product had the following average formula where the sum of the subscripts equals four for any given compound:

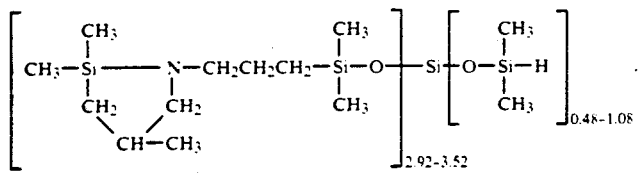

EXAMPLE 5

Reaction of a Trimethylsiloxy Endblocked Poly(co-dimethylsiloxane-methylhydrogensiloxane) with 1,1,4-Trimethyl-2-allyl-2-aza-silacyclopentane To each of two small vials was charged with 2.00 g of trimethylsiloxy endblocked poly(co-dimethylsiloxane-methylsiloxane) having an average of 10 siloxane units and 0.768 weight percent of silicon-bonded hydrogen, 1.93 g of 1,1,4-trimethyl-2-allyl-2-aza-silacyclopentane for sample 1 and 2.58 g 1,1,4-trimethyl-2-allyl-2-aza-silacyclopentane for sample 2. Sample 1 had a molar ratio of SiH to aza-silacyclopentane of 1:0.75 and Sample 2 had a molar ratio of SiH to aza-silacyclopentane of 1:1. To each vial, 0.02 g of the platinum catalyst of Example 2 was added and the vials were then sealed and placed in a 140° C. oil bath. After 30 min. the contents were analyzed by $^{29}$Si NMR. The fraction of hydrosilated 1,1,4-trimethyl-2-allyl-2-aza-silacyclopentane relative to addition product of 1,1,4-trimethyl-2-allyl-2-aza-silacyclopentane times the theoretical maximum percent hydrosilated was used to determine the percent substitution. The functionality was calculated assuming an initial SiH functionality of 5.4. Sample 1 resulted in 53% of the SiH reacting and the functionality was 2.9 aza-silacyclopentane groups per molecule and Sample 2 resulted in 62% of the SiH reacting and the functionality was 3.4 aza-silacyclopentane groups per molecule. A $^{29}$Si NMR of Sample 2 of the crude mixture was: 18.0 (0.38), rearranged 1,1,4-trimethyl-2-allyl-2-aza-silacyclopentane; 14.5 (0.62), hydrosilated 1,1,4-trimethyl-2-allyl-2-aza-silacyclopentane which has the formula

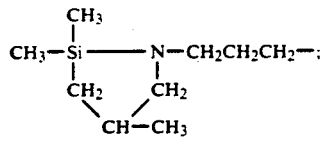

10 to 7, (0.52), SiMe$_3$; −18 to −23 (1.74), SiMeRO and SiMe$_2$O; −36 to −38 (0.74), residual SiMeHO. The average formula for the product of Sample 2 was

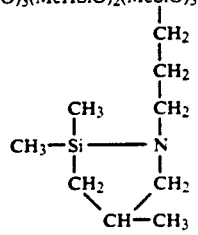

EXAMPLE 7

Reaction of Tetramethylcyclotetrasiloxane with 1,1,4-Trimethyl-2-allyl-2-aza-silacyclopentane A small vial was charged with 2.00 g of tetramethylcyclotetrasiloxane and an equal molar amount of 1,1,4-trimethyl-2-allyl-2-aza-silacyclopentane. About 0.02 g of the platinum catalyst of Example 2 was added and the vial was sealed and placed in a 140° C. oil bath. After 30 minutes, the contents was analyzed by $^{29}$Si NMR which showed that 72 percent of the SiH had reacted. The product had a representative formula

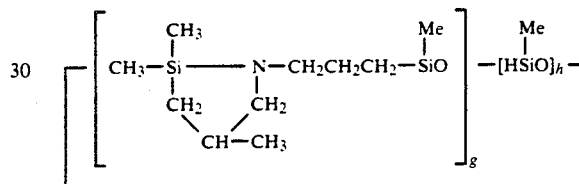

Where the sum of g and h was equal to four and g was about 2.9.

EXAMPLE 8

Reaction of Pentamethylcyclopentasiloxane with 1,1,4-Trimethyl-2-allyl-2-aza-silacyclopentane A 50 ml round-bottom flask with magnetic stirrer and addition funnel containing 16.2 g (95.6 mmol) of 1,1,4-trimethyl-2-allyl-2-aza-silacyclopentane was charged with 4.60 g (15.3 mmol) of pentamethylcyclopentasiloxane. To this was added 0.03 g of a platinum complex chloroplatinic acid and symdivinyltetramethylsiloxane and about 2 g of 1,1,4-trimethyl-2-allyl-2-aza-silacyclopentane. The flask containing the reaction mixture was placed in a 120° C. oil bath for 10 minutes and the remaining 1,1,4-trimethyl-2-allyl-2-aza-silacyclopentane was added dropwise over a one hour period. The mixture was stirred at 120° C. for two hours, at 130° C. for one hour, and then stripped up to 150° C. at 0.1 mmHg to yield 17.65 g (101%) of a product of the following average formula

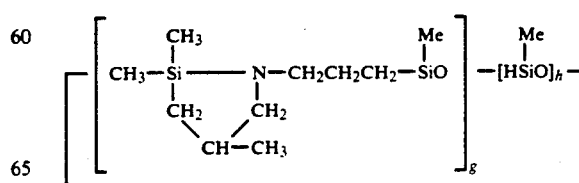

Where the sum of g and h was equal to five.

EXAMPLE 9

Reaction of 1,1,3,3-Tetramethyldisiloxane with a 2:1 Mixture of 1-Allyl-6,6-dimethyl-6-sila-2-piperidone and 1-Allyl-4,5,5-trimethyl-5-sila-2-pyrrolidone The mixture of 1-allyl-6,6-dimethyl-6-sila-2-piperidone and 1-allyl-4,5,5-trimethyl-5-sila-2-pyrrolidone was first prepared in the following manner. 112.5 Grams of dimethylchlorosilane was slowly added to a solution of 142.48 g (0.900 mol) of the trimethylsilyl ester of vinylacetic acid and 0.05 g of a chloroplatinic acid complex with sym-divinyltetramethyldisiloxane having a platinum content of about 0.7 weight percent in 140 g of toluene while heating between 90° C. to 120° C. After the addition, 129 g of thionyl chloride was slowly added at reflux. A small amount of yellowish precipitate formed. The toluene, excess thionyl chloride, and trimethylchlorosilane were distilled at reduced pressure. The product was distilled at 68° C. to 69° C. and 0.05 mmHg to yield 144 g (73%) of product, which was a mixture of 4-chlorodimethylsilylbutanoic acid chloride and 3-chlorodimethylsilylbutanoic acid chloride. 17.73 Grams of allylamine was slowly added with cooling and stirring to a solution of 22.27 g (0.1035 mol) of the mixture of above butanoic acid chlorides in 200 ml of diethyl ether. An extremely exothermic reaction occurred with the formation of solid allylammonium chloride which was removed by filtration. The ether was removed at room temperature under vacuum. The residue was distilled at 76° C. and 0.03 mmHg to yield 15.50 g (75.1%) of a 2:1 weight ratio of

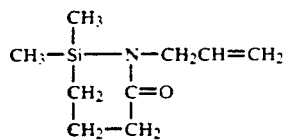
(C)

to

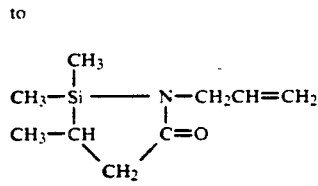
(B)

A dry 50 ml three-necked, round-bottom flask fitted with a thermometer and condenser was charged with 4.20 g (31.3 mmol) of tetramethyldisiloxane, 0.1 g of the platinum complex as defined above, and 12.61 g of the mixture of 1-allyl-6,6-dimethyl-6-sila-2-piperidone and 1-allyl-4,5,5-trimethyl-5-sila-2-pyrrolidone. After heating at 110° C. to 140° C. for 12 hours. The excess starting material was distilled at reduced pressure to yield 15.84 g of an amber liquid. The product had a general formula

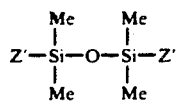

in which Z' was a 2:1 mixture of the following groups

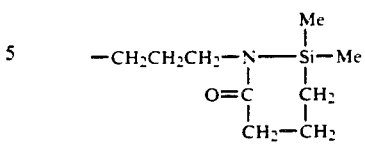

and

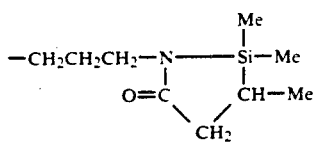

respectively.

EXAMPLE 10

For each moisture curable composition, there was first prepared a base mixture of 50 parts of a hydroxyl endblocked polydimethylsiloxane having a viscosity of 50 Pa.s at 25° C. and 50 parts of precipitated calcium carbonate filler. For each composition, 150 parts of the base mixture was charged into a Semco Semkit mixer under anhydrous conditions. To each base mixture, chain extender and crosslinker were added in the parts as described in Table III, IV, and V, by injecting into the middle of the base in the Semkit tube using the Semkit plunger. The resulting mixture was mixed for 10 minutes and then centrifuged to remove entrapped air. The mixture was then extruded under 90 psi of air pressure for 15 seconds and the amount extruded was weighed and multipled by four to measure the extrusion rate. The mixture was drawn down to 80 mil thickness and placed in a room with a 44% relative humidity and a temperature of 22° C. The skin over time was determined to be the time at which no mixture stuck to a finger lightly placed on the surface. The tack free time was determined by 28.4 g, 2 inch by 1 inch weight on a 2 mil polyethylene sheet on the mixture for 5 seconds and slowly peeling off at 180 degrees. The tack free time is when no transfer of material to the polyethylene sheet occurs. Tensile properties and durometers were measured using ASTM methods after aging for two weeks.

In Table III, the chain extender used was the one prepared in Example 2 and the crosslinker used was the one prepared in Example 7.

In Table IV, the chain extender used was the one prepared in Example 2 in the amount of 7.60 parts and the crosslinker used was the one prepared in Example 7 in the amount shown in Table IV, but stannous octoate, in the amounts shown in Table IV was used as a curing catalyst.

In Table V, the chain extender used was the one prepared in Example 2 in the amount of 7.60 parts and the crosslinker used was the one prepared in Example 5 in the amount shown in Table V.

TABLE III

| COMPO-SITION NO. | WEIGHT CHAIN EXTENDER parts | WEIGHT CROSS-LINKER parts | EXTRU-SION RATE g/min | SKIN OVER TIME sec | TACK FREE TIME sec | DUROMETER SHORE A | TENSILE STRENGTH AT BREAK psi | ELONGATION AT BREAK % | 150% MODULUS psi |
|---|---|---|---|---|---|---|---|---|---|
| 1 | 7.60 | 1.53 | 81 | 118 | 118 | 7 | 35 | 745 | 17.4 |
| 2 | 7.60 | 1.93 | 60 | 103 | 103 | 9 | 52 | 654 | 21.6 |
| 3 | 7.60 | 2.70 | 94 | 13 | 42 | 16 | 125 | 526 | 46.3 |
| 4 | 7.60 | 4.50 | 82 | 2 | 11 | 21 | 150 | 371 | 68.1 |
| 5 | 7.60 | 6.75 | 94 | 3 | 6 | 25 | 103 | 164 | — |
| 6 | 7.60 | 9.00 | 73 | 1 | 2.5 | 20 | 88 | 99 | — |
| 7 | 7.60 | 13.51 | 108 | 1 | 2 | 22 | 74 | 71 | — |
| 8 | 5.20 | 1.05 | 61 | 66 | 0 | 5 | 38 | 824 | 17.7 |
| 9 | 5.20 | 1.32 | 65 | 51 | 98 | 9 | 63 | 680 | 22.5 |
| 10 | 5.20 | 1.85 | 51 | 19 | 19 | 12 | 115 | 595 | 38.4 |
| 11 | 5.20 | 3.08 | 49 | 5 | 7 | 20 | 156 | 375 | 71.8 |
| 12 | 5.20 | 4.63 | 53 | 2 | 7 | 23 | 165 | 308 | 89.1 |
| 13 | 5.20 | 6.17 | 60 | 1 | 4 | 21 | 142 | 189 | 114.5 |
| 14 | 5.20 | 9.25 | 63 | 1 | 3 | 0 | 0 | 0 | — |
| 15 | 2.60 | 0.52 | 14 | 1 | 1 | 10 | 46 | 685 | 20.1 |
| 16 | 2.60 | 0.66 | 12 | 9 | 9 | 10 | 74 | 676 | 29.0 |
| 17 | 2.60 | 0.93 | 0 | 1 | 1 | 13 | 107 | 558 | 40.3 |
| 18 | 2.60 | 1.54 | 0 | 0.5 | 0.5 | 18 | 144 | 425 | 64.2 |
| 19 | 2.60 | 2.31 | 21 | 1 | 2 | 22 | 177 | 421 | 87.1 |
| 20 | 2.60 | 3.08 | 7 | 0.5 | 0 | 20 | 160 | 245 | 111.6 |
| 21 | 2.60 | 4.63 | 30 | 0.5 | 1 | 24 | 164 | 205 | 114.3 |

Table III shows that a variety of amounts of crosslinker and chain extender can be used to produce cured products with a variety of properties.

TABLE IV

| COMPO-SITION NO. | WEIGHT CROSS-LINKER parts | STANNOUS OCTOATE CATALYST parts | EXTRU-SION RATE g/min | SKIN OVER TIME sec | TACK FREE TIME sec | DUROMETER SHORE A | TENSILE STRENGTH AT BREAK psi | ELON-GATION AT BREAK % | MODULUS 150% psi |
|---|---|---|---|---|---|---|---|---|---|
| 22 | 1.93 | 0.00 | 43 | 17 | 58 | 7 | 69 | 587 | 34.2 |
| 23 | 1.93 | 0.10 | 21 | 2 | 5 | 8 | 47 | 450 | 26.2 |
| 24 | 1.93 | 0.50 | GELLED | — | — | — | — | — | — |
| 25 | 2.70 | 0.00 | 97 | 8 | 17 | 10 | 107 | 508 | 40.8 |
| 26 | 2.70 | 0.05 | 70 | 4 | 9 | 11 | 129 | 434 | 55.5 |
| 27 | 2.70 | 0.10 | 47 | 3 | 5 | 12 | 119 | 463 | 50.2 |
| 28 | 2.70 | 0.50 | GELLED | — | — | — | — | — | — |

Table IV shows that the use of a catalyst can reduce the skin over time and the tack free time, but caution is required because the resulting product may gel before test pieces can be made for measurement of properties.

TABLE V

| COMPOSITION NO. | WEIGHT CROSS-LINKER parts | EXTRUSION RATE g/min | SKIN OVER TIME sec | TACK FREE TIME sec | DUROMETER SHORE A | TENSILE STRENGTH AT BREAK psi | ELONGATION AT BREAK % | MODULUS 150% psi |
|---|---|---|---|---|---|---|---|---|
| 29 | 6.11 | 91 | 4 | 9 | 12 | 79.6 | 287 | 46.6 |
| 30 | 3.67 | 88 | 4.5 | 5 | 3 | 50.3 | 476 | 20.7 |
| 31 | 2.62 | 87 | 8 | 19 | 1 | 24.7 | 601 | 10.5 |
| 32 | 2.07 | 84 | 10 | 150 | — | — | — | — |
| 33 | 1.83 | 106 | 17 | 156 | — | — | — | — |

Table V shows that cured products can be obtained with another combination of crosslinker and chain extender to make useful materials.

EXAMPLE 11

A one package composition was prepared by charging a small vial with 10 parts of a hydroxyl endblocked polydimethylsiloxane having an average of 322 dimethylsiloxane units per molecule and 4.8 parts of the product of Example 8. After mixing for about one minute, a viscous opaque mixture resulted. This mixture gelled in an atmosphere of 44% relative humidity and 68° F. within 3 minutes to an elastomeric material. A sample of the mixture in a vial sealed from atmospheric moisture did not change after storage for five months.

EXAMPLE 12

A two package product was prepared by making Part (I) in a mixing tube which can be sealed from atmospheric moisture (a SEMCO tube), 50 parts of a hydroxyl endblocked polydimethylsiloxane having an average of 322 dimethylsiloxane units per molecule with 19.84 parts of an aza-silacyclopentane similar to the aza-silacyclopentane of Example 7, except g had a value of 3.55. The resulting mixture was mixed for 8 minutes and centrifuged. Part (II) of this two package product was the hydroxyl endblocked polydimethylsiloxane having an average of 322 dimethylsiloxane units per molecule.

One part of (II) was mixed with 19 parts of (I) in a vial. After throughly mixing (I) and (II), the vial was sealed. Within six minutes the composition exhibited deep section cure and after two hours, a tack free elastomer resulted.

EXAMPLE 13

A two package product was prepared. Package (I) was made in a mixing tube which prevents moisture from contacting the mixture which was charged with 50 parts of a hydroxyl endblocked polydimethylsiloxane having an average of 322 dimethylsiloxane units per molecule. 5.94 parts of disiloxane product of Example 2, and 2.11 parts of the aza-silacyclopentane as described in Example 12. The resulting mixture was mixed for 8 minutes and then centrifuged.

Package (II) was made by mixing 50 parts of a hydroxyl endblocked polydimethylsiloxane having an average of 322 dimethylsiloxane units per molecule, 6.89 parts of a hydroxyl endblocked polydimethylsiloxane having an average of 7 dimethylsiloxane units per molecule and 0.23 part of water. The resulting mixture was mixed for 8 minutes and then centrifuged to produce a homogeneous mixture.

Equal parts of package (I) and package (II) were mixed and delivered to a vial which was sealed. After six minutes, the resulting mixture had cured to an elastomeric material throughout its depth.

EXAMPLE 14

Compositions were prepared by mixing 15 parts of a hydroxyl endblocked polydimethylsiloxane having the average number of dimethylsiloxane units per molecule as shown in Table VI with the amount of the disiloxane product prepared in Example 2. After the disiloxane product and polydimethylsiloxane were throughly mixed, the product of Example 7, a crosslinker, was added and blended in and the air was removed under vacuum. The amount of crosslinker was as shown in Table VI. Samples were prepared by pouring the mixture into a 60 mil chase at 0% relative humidity. The sample was then exposed to 44% relative humidity at 23° C. and the skin over time was observed. The tensile strength, elongation, and modulus were measured after two weeks exposure at 23° C. and 44% relative humidity. The results were as shown in Table VI where values of zero indicate that the material could not be handled to perform the property measurement and values of NA indicate that the data is not available.

TABLE VI

| COMPOSITION NO. | NUMBER OF DIMETHYL SILOXANE UNITS | WEIGHT CHAIN EXTENDER parts | WEIGHT CROSS-LINKER parts | SKIN OVER TIME sec | TENSILE STRENGTH AT BREAK psi | YOUNG'S MODULUS psi | ELON-GATION AT BREAK % | MODULUS 100% psi | MODULUS 200% psi |
|---|---|---|---|---|---|---|---|---|---|
| 34 | 322 | 0.891 | 0.720 | 23 | 11.4 | 4.2 | 551 | 3.2 | 5 |
| 35 | 322 | 2.672 | 0.432 | 38 | 0 | 0 | 0 | 0 | 0 |
| 36 | 236 | 1.215 | 0.982 | 20 | 37.5 | 8.3 | 766 | 4.4 | 6.3 |
| 37 | 236 | 2.430 | 0.589 | 37 | 6.1 | 1.3 | 792 | 1.1 | 1.3 |
| 38 | 236 | 1.215 | 0.196 | 29 | 0 | 0 | 0 | 0 | 0 |
| 39 | 196 | 2.925 | 1.183 | 17 | 14.3 | 5.5 | 310 | 4.3 | 8.3 |
| 40 | 322 | 0.891 | 0.432 | 7 | 23.1 | 8.3 | 806 | 4.6 | 6.2 |
| 41 | 196 | 4.388 | 0.710 | 35 | 0 | 0 | 0 | 0 | 0 |
| 42 | 236 | 3.645 | 0.982 | 37 | 9.8 | 3.1 | 440 | 2.4 | 4.4 |
| 43 | 322 | 1.782 | 0.720 | 23 | 10.7 | 2.9 | 435 | 2.4 | 4.3 |
| 44 | 196 | 2.925 | 0.237 | 58 | NA | NA | NA | NA | NA |
| 45 | 322 | 1.782 | 0.144 | 3 | 6.8 | 12.2 | 68.2 | 6.4 | 12.3 |

The compositions 34-45 cured to weak elastomeric material with low modulus. Those compositions which cured to products which could not be handled may be useful as encapsulating gels.

EXAMPLE 15

Compositions were prepared by mixing 50 parts of a hydroxyl endblocked polydimethylsiloxane having an average of about 600 dimethylsiloxane units per molecule with 2.97 parts of the disiloxane product of Example 2 (chain extender) for a period of five minutes and then an amount, as shown in Table VII, of the product of Example 7 or 8 was added with a catalyst as shown in Table VII and mixed to produce a homogeneous mixture. Air was removed from the resulting mixture by centrafuging. Samples of these compositions were poured into 60 mil chases at 0% relative humidity. The skin over time was determined by exposing the samples to 44% relative humidity at 23° C. The physical properties were measured after a two week exposure to 23° C. and 44% relative humidity. The results were as shown in Table VII.

TABLE VII

| COMPOSITION NO. | CROSSLINKER EX. 7 parts | CROSSLINKER EX. 8 parts | CATALYST/ parts | SKIN OVER TIME sec | TENSILE STRENGTH AT BREAK psi | ELON-GATION AT BREAK % | YOUNG'S MODULUS psi | MODULUS 100% psi | MODULUS 200% psi |
|---|---|---|---|---|---|---|---|---|---|
| 46* | 3.95 | 0 | dibutyltin dilaurate/ 0.12 | 6 | 26.4 | 606 | 10.7 | 5.6 | 8.4 |
| 47* | 0 | 2.43 | none | 9 | 25.5 | 660 | 11.6 | 6.5 | 8.8 |
| 48* | 1.92 | 0 | none | 14 | 21.2 | 579 | 10.6 | 5.9 | 8.4 |
| 49* | 1.83 | 0 | 2,5-di-iso-proproxy-bis ethylaceto-acetate titanium/0.12 | 14 | NA | NA | NA | NA | NA |
| 50* | 1.88 | 0 | tetrabutyl titanate/ 0.058 | 12 | 20.7 | 541 | 12.8 | 7.3 | 10.2 |
| 51* | 7.68 | 0 | none | 3 | 32.9 | 177 | 28.5 | NA | NA |
| 52* | 1.92 | 0 | none | 6 | 25.2 | 577 | 16.2 | 9.0 | 13.1 |
| 53** | 1.92 | 0 | none | 2 | 39.2 | 204 | 39.5 | 26.1 | NA |

TABLE VII-continued

| COMPO-SITION NO. | CROSSLINKER EX. 7 parts | EX. 8 parts | CATALYST/ parts | SKIN OVER TIME sec | TENSILE STRENGTH AT BREAK psi | ELON-GATION AT BREAK % | YOUNG'S MODULUS psi | MODULUS 100% psi | MODULUS 200% psi |
|---|---|---|---|---|---|---|---|---|---|
| 54** | 0.97 | 0 | none | 1 | 24.4 | 274 | 22.0 | 9.4 | 20.2 |
| 55** | 0.48 | 0 | none | 3 | 25.0 | 916 | 10.3 | 5.5 | 8.1 |
| 56** | 1.88 | 0 | stannous octoate/0.12 | 3 | 31.6 | 817 | 13.2 | 7.7 | 10.2 |

*Chain extender was added first and then the crosslinker.
**A mixture of the chain extender and crosslinker was made and the mixture was then added to the hydroxyl endblocked polydiorganosiloxane.

That which is claimed is:

1. A silicon compound comprising at least one silicon atom to which is bonded at least two heterocyclic Si—N groups having one heterocyclic silicon atom, at least one nitrogen atom, and three to five ring carbon atoms wherein at least one nitrogen atom is bonded to the heterocyclic silicon atom and either a nitrogen atom or the heterocyclic silicon atom is bonded to the silicon atom through a divalent saturated aliphatic hydrocarbon radical.

2. The silicon compound according to claim 1 in which the heterocyclic Si—N groups are silicon-bonded Si—N groups selected from the group consisting of

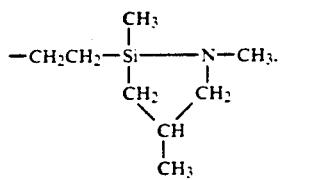

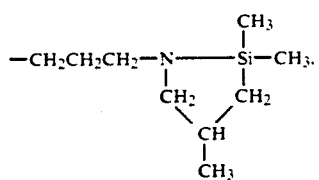

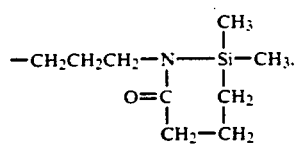

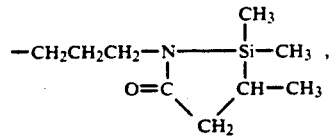

and

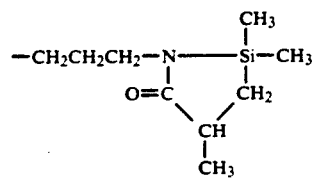

and the remaining groups bonded to the silicon atoms of the silicon compound are selected from the groups consisting of divalent oxygen atoms, divalent hydrocarbon radicals, and monovalent hydrocarbon radicals.

3. The silicon compound according to claim 1 in which there are two heterocyclic Si—N groups per molecule.

4. The silicon compound according to claim 3 in which the compound has a formula selected from the group consisting of ZMe$_2$SiO(Me$_2$SiO)$_y$SiMe$_2$Z.
ZMe$_2$Si—X—SiMe$_2$Z.
and

where Z is a heterocyclic Si—N group, R is a monovalent hydrocarbon group, X is a divalent hydrocarbon radical selected from the group consisting of —(CH$_2$)$_m$— or —C$_6$H$_4$—, y is $\geq 0$, and m is 2 to 6 inclusive.

5. The silicon compound according to claim 1 in which there is at least three heterocyclic Si—N groups per molecule.

6. The silicon compound according to claim 5 in which the compound has a formula selected from the group consisting of Si(OSiMe$_2$Z')$_4$.    RSi(OSiMe$_2$Z')$_3$.    

Me$_3$SiO(Me$_2$SiO)$_y$(MeZ'SiO)$_n$SiMe$_3$.

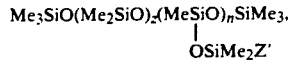

and

Z'Me$_2$SiO(Me$_2$SiO)$_y$(MeZ'SiO)$_n$SiMe$_2$Z' where each Z' is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$.

7. The silicon compound according to claim 2 in which there are two heterocyclic Si—N groups per molecule.

8. The silicon compound according to claim 7 in which the compound has a formula selected from the group consisting of ZMe$_2$SiO(Me$_2$SiO)$_y$SiMe$_2$Z.
ZMe$_2$Si—X—SiMe$_2$Z.
and -continued

where Z is a heterocyclic Si—N group, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive.

9. The silicon compound according to claim 2 in which there are at least three heterocyclic Si—N groups per molecule.

10. The silicon compound according to claim 9 in which the compound has a formula selected from the group consisting of

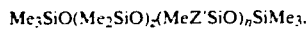

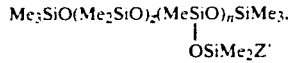

and

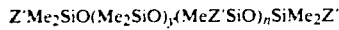

where each Z' is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$.

11. A composition comprising a product which is storage stable in a package when protected from moisture but polymerizes when removed from the package and exposed to moisture and further comprising a silicon compound comprising at least one silicon atom to which is bonded at least two heterocyclic Si—N groups having one heterocyclic silicon atom, at least one nitrogen atom, and three to five ring carbon atoms wherein at least one nitrogen atom is bonded to the heterocyclic silicon atom and either a nitrogen atom or the heterocyclic silicon atom is bonded to the silicon atom through a divalent saturated aliphatic hydrocarbon radical.

12. The composition according to claim 11 in which the heterocyclic Si—N groups of the silicon compound are siliconbonded Si—N groups selected from the group consisting of

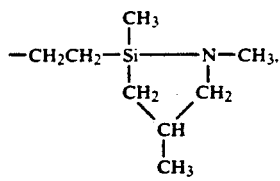

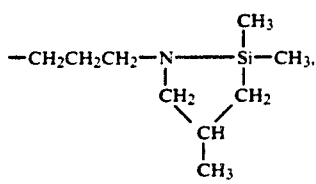

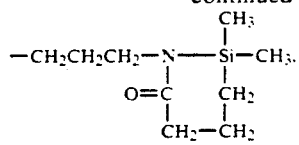

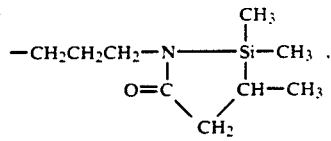

and

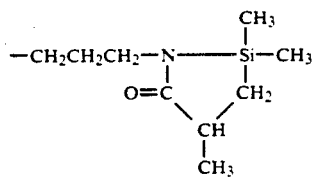

and the remaining groups bonded to the silicon atoms of the silicon compound are selected from the groups consisting of divalent oxygen atoms, divalent hydrocarbon radicals, and monovalent hydrocarbon radicals.

13. The composition according to claim 11 in which there is a mixture of silicon compounds where there are silicon compounds with two heterocyclic Si—N groups per molecule and there are silicon compounds with at least three heterocyclic Si—N groups per molecule.

14. The composition according to claim 13 in which the silicon compounds with two heterocyclic Si—N groups per molecule are compounds having a formula selected from the group consisting of

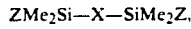

and

where Z is a heterocyclic Si—N group, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive and the silicon compounds with at least three heterocyclic Si—N groups per molecule are compounds having a formula selected from the group consisting of

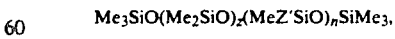

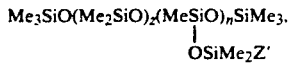

and

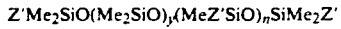

where each Z' is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$.

15. The composition according to claim 14 in which the heterocyclic Si—N group is selected from the group consisting of

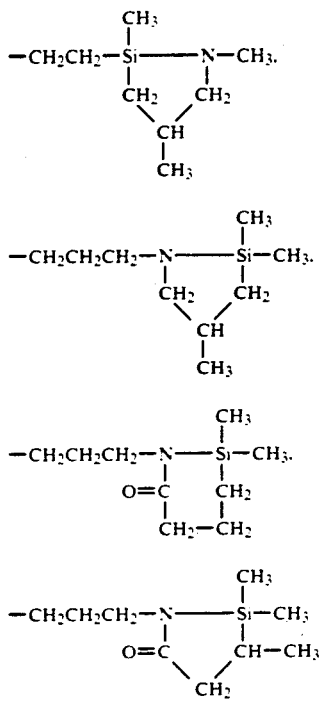

and

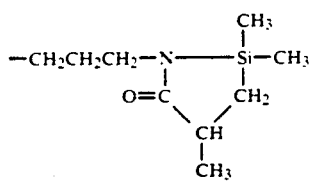

and the remaining groups bonded to the silicon atoms of the silicon compound are selected from the groups consisting of divalent oxygen atoms, divalent hydrocarbon radicals, and monovalent hydrocarbon radicals.

16. The compositions according to claim 11 in which the product is made by mixing (A) crosslinkers of the present invention having a formula selected from the group consisting of

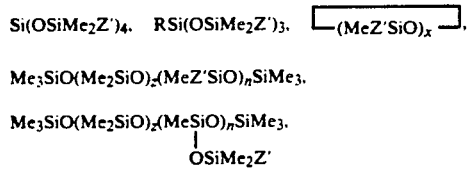

and $$Z'Me_2SiO(Me_2SiO)_y(MeZ'SiO)_nSiMe_2Z'$$

where each Z' is a heterocyclic Si—N group or a hydrogen atom where the number of heterocyclic Si—N groups per molecule is greater than 2, R is a monovalent hydrocarbon radical, z is an integer of from 3 to 10, y is $\geq 0$, and n is $\geq 3$ with (B) silanol functional siloxane which is selected from the group consisting of a linear polydiorganosiloxane represented by the following formula $$HO(R_2SiO)_dH$$

where R is a monovalent hydrocarbon radical, and d has an average value of from 1 to 1,000; with a silicone resin represented by the formula $$(SiO_2)_f(RSiO_{1.5})_g(R_2SiO)_h(R_3SiO_{0.5})_i(OH)_j$$

where R is defined above and the values of f, g, h, and i being such that the ratio of R/Si is in the range of 0.5 to 1.8 and the value of j is such that there is at least two silicon-bonded hydroxyl groups per molecule; and mixtures thereof, where (A) and (B) are present in amounts such that the molar ratio of the heterocyclic Si—N group per silanol group (Si—OH) is in the range of 2:1 to 50:1.

17. The composition according to claim 16 in which the product further comprises a chain extender selected from the group consisting of $$ZMe_2SiO(Me_2SiO)_ySiMe_2Z,$$

$$ZMe_2Si—X—SiMe_2Z,$$

and

where Z is a heterocyclic Si—N group, R is a monovalent hydrocarbon group, X is a divalent hydrocarbon radical selected from the group consisting of —(CR$_2$)$_m$— or —C$_6$H$_4$—, y is $\geq 0$, and m is 2 to 6 inclusive.

18. A two package composition where (I) one package is the product as described in claim 16 and (II) a second package is the silanol functional siloxane (B) of claim 16 where the ratio of (I) to (II) is such that the number of silanol groups in (II) approximates the number of heterocyclic Si—N groups in (I).

19. The two package composition according to claim 18 in which the second package (II) also contains water and the number silanol plus OH from the water is sufficient to cure a mixture of (I) and (II) without atmospheric moisture.

* * * * *